US012217233B2

(12) United States Patent
Christiansen (10) Patent No.: US 12,217,233 B2
(45) Date of Patent: Feb. 4, 2025

(54) HEARING DEVICE FOR SUBSCRIPTION SERVICE

(71) Applicant: GN Hearing A/S, Ballerup (DK)

(72) Inventor: Kim Kris Christiansen, Ballerup (DK)

(73) Assignee: GN HEARING A/S, Ballerup (DK)

( * ) Notice: Subject to any disclaimer, the term of this patent is extended or adjusted under 35 U.S.C. 154(b) by 326 days.

(21) Appl. No.: 17/700,397

(22) Filed: Mar. 21, 2022

(65) Prior Publication Data

US 2022/0343304 A1 Oct. 27, 2022

(30) Foreign Application Priority Data

Apr. 27, 2021 (DK) .................................. 202170188
Apr. 27, 2021 (EP) ..................................... 21170582

(51) Int. Cl.
*H04R 25/00* (2006.01)
*G06Q 20/12* (2012.01)
*G16H 40/40* (2018.01)

(52) U.S. Cl.
CPC .......... *G06Q 20/127* (2013.01); *G16H 40/40* (2018.01); *H04R 25/30* (2013.01); *H04R 25/554* (2013.01); *H04R 2225/39* (2013.01); *H04R 2225/55* (2013.01)

(58) Field of Classification Search
CPC ....................... H04R 2225/39; H04R 2225/55; H04R 25/30; H04R 25/554; H04R 2225/51; H04R 25/55
USPC ........................................................ 381/312
See application file for complete search history.

(56) References Cited

U.S. PATENT DOCUMENTS

| 6,785,394 B1 * | 8/2004 | Olsen ................... H04R 25/505 381/323 |
| 8,767,986 B1 | 7/2014 | Fabry et al. |
| 2004/0039604 A1 * | 2/2004 | Tallal, Jr. ............... G06Q 30/02 705/2 |
| 2004/0078234 A1 * | 4/2004 | Tallal, Jr. ............... G06Q 30/02 705/2 |
| 2004/0078235 A1 * | 4/2004 | Tallal, Jr. ............... G06Q 30/02 705/2 |
| 2014/0247109 A1 | 9/2014 | Curry |

(Continued)

FOREIGN PATENT DOCUMENTS

WO  WO 2017/005326  1/2017

OTHER PUBLICATIONS

Extended EP Search Report dated Oct. 18, 2021 for EP application No. 21170582.7.

(Continued)

*Primary Examiner* — Phylesha Dabney
(74) *Attorney, Agent, or Firm* — Vista IP Law Group, LLP (57) ABSTRACT

Disclosed is a hearing device configured to be arranged at a user's ear, the hearing device comprising: an input transducer for generating one or more input signals based on a received audio signal; a signal processor configured for processing the one or more input signals; an output transducer for providing an audio output signal based on an output signal from the signal processor; wherein the hearing device comprises a time monitor for monitoring an expiry time of a subscription for the hearing device provided by a subscription server, wherein the hearing device is configured to perform an action when the time monitor detects that the expiry time of the subscription is reached.

29 Claims, 6 Drawing Sheets

Initial setup of hearing device (56) References Cited

U.S. PATENT DOCUMENTS

| | | |
|---|---|---|
| 2016/0134742 A1 | 5/2016 | Shennib |
| 2020/0098475 A1 | 3/2020 | Westermann et al. |
| 2020/0267482 A1 | 8/2020 | Westermann et al. |

OTHER PUBLICATIONS

Examination report dated Oct. 27, 2021 for Danish patent application No. PA 2021 70188.

* cited by examiner

HEARING DEVICE FOR SUBSCRIPTION SERVICE

RELATED APPLICATION DATA

This application claims priority to, and the benefit of, Danish Patent Application No. PA 202170188 filed on Apr. 27, 2021, and European Patent Application No. 21170582.7 filed on Apr. 27, 2021. The entire disclosures of the above applications are expressly incorporated by reference herein.

FIELD

The present disclosure relates to a method, a system, a subscription server, a computer program product and a hearing device configured to be arranged at a user's ear. The hearing device comprises an input transducer for generating one or more input signals based on a received audio signal. The hearing device comprises a signal processor configured for processing the one or more input signals. The hearing device comprises an output transducer for providing an audio output signal based on an output signal from the signal processor. The hearing device comprises a time monitor for monitoring an expiry time of a subscription for the hearing device provided by a subscription server.

BACKGROUND

Today, hearing aid users are often prevented from gaining access to the most relevant hearing aid solution due to financial limitations. Furthermore, the hearing care providers (HCPs) are prevented from gaining the mark-up they could otherwise get from a high-end solution, because customers do not have the financial capability needed to invest in the best solution.

Thus, there is a need for an improved hearing device and related systems and methods, for providing access for the hearing device users to the most relevant hearing aid solutions.

SUMMARY

Disclosed is a hearing device configured to be arranged at a user's ear. The hearing device comprises an input transducer for generating one or more input signals based on a received audio signal. The hearing device comprises a signal processor configured for processing the one or more input signals. The hearing device comprises an output transducer for providing an audio output signal based on an output signal from the signal processor. The hearing device comprises a time monitor for monitoring an expiry time of a subscription for the hearing device provided by a subscription server. The hearing device is configured to perform an action when the time monitor detects that the expiry time of the subscription is reached.

It is an advantage that the hearing device comprises a time monitor for monitoring an expiry time of a subscription for the hearing device, because when the time monitor detects that the expiry time of the subscription is reached, then the hearing device is configured to perform an action.

The subscription of the hearing device may be with a subscription provider. The subscription may be handled and/or operated by a subscription server. The subscription server may provide the expiry time of the subscription.

The subscription may be for providing the specified or normal functioning of the hearing device and/or the subscription may be for receiving hearing device updates, improvements etc.

The subscription may be paid on a regular basis, e.g. like leasing, thus instead of buying the hearing device and owning it, the user may lease, such as subscribe to the hearing device and/or the hearing device functionality. Thus the hearing device user may regularly pay a subscription payment.

The subscription server may be a cloud server, a remote server etc. The subscription server may be owned and controlled by the hearing device manufacturer. The subscription server may be operated by the hearing device manufacturer. The hearing care providers (HCPs) may have access to the subscription server to service their particular customers, i.e. the hearing device users.

The subscription service may comprise periodic subscription payment to be paid by the hearing device user.

The hearing device comprises a time monitor for monitoring an expiry time of a subscription for the hearing device provided by a subscription server. The time monitor may be a time keeper or a time tracker or a timer. The expiry time may be an interval or period from the latest subscription payment to the next subscription payment.

The hearing device is configured to perform an action when the time monitor detects that the expiry time of the subscription is reached.

Thus, the hearing device has a time monitor which may keep tracks of time, and when the time monitor detects that the expiry time of the subscription is reached, e.g. the new payment for subscription is due, e.g. after 30 days, 3 months, 6 months, 1 year, 2 years, 3 years etc, after the last subscription payment, then the hearing device performs an action.

The action can be different options, e.g. the hearing device stops functioning, or the hearing device only functions in a limited way, and/or the user receives reminders about renewing the subscription etc.

The hearing device may be connected/paired with a software application, a so-called an app, such as a subscription app, on an associated smartphone of the user. Thus the communication with the subscription server may be performed via the app. The hearing device may not communicate directly with the subscription server as this may require a lot of electric power, which may not be suitable for a hearing device which is running on limited battery power.

If the subscription is paid before the expiry time, e.g. the expiry time of the subscription is not reached before the payment is made, then the hearing device may continue to operate as normally.

It is an advantage of the disclosed hearing device that it solves a problem which hearing device users may encounter today. Because hearing devices, such as hearing aids, especially advanced and high-end hearing aids, may be expensive for the hearing aid user to buy. Hearing aid users may finance their hearing aids through loans or by offering of alternative payment schemes between the hearing care professional (HCP) and the hearing aid users.

Furthermore, today hearing aid users are often prevented from gaining access to the most relevant hearing aid solution due to financial limitations. Furthermore, the hearing care providers (HCPs) are prevented from gaining the mark-up they could otherwise get from a high-end solution, because customers do not have the financial capability needed to invest in the best solution. Finally, future improvements of hearing aid services are likely to rely on access to data related to use of hearing aids.

It is an advantage of the present hearing devices and the related aspects, that for the hearing device end-user access to health becomes more affordable. For the HCPs closer interaction with end-users reduce return rates and increase customer loyalty. For the hearing device manufacturer, increased access to data improves foundation for future service offerings and lowering the up-front investment improves the chance of selling high-end hearing aids. For markets where hearing aids are publicly sponsored, the health benefits per public spending will improve as adoption rates improve.

As an alternative to the present solution, end-users may finance their hearing aids through loans or by offering alternative payment schemes between the HCP and the end-users. However, this alternative solution cannot ensure the support elements or provide the data capture as in the presented solution.

In the present solution, hearing aids may be handled as a service, this approach is known from leasing, selling and financing other expensive consumer goods like cars, smartphones etc. In case the end-user does not perform the agreed payment, it may potentially be an option to either stop the hearing aid from functioning, or reduce the quality of service of the hearing aid, for example via an associated app.

The hearing device is configured to be arranged at a user's ear. The hearing device may be arranged inside the user's ear. The hearing device may be arranged behind the user's ear. The hearing device may be arranged in the user's ear. The hearing device may be arranged at a close vicinity of the user's ear. The hearing device may have a component adapted to be arranged behind the user's ear and a component adapted to be arranged in the user's ear.

The hearing device comprises an input transducer for generating one or more input signals based on a received audio signal. An example of an input transducer is a microphone.

The hearing device comprises a signal processor configured for processing the one or more input signals. The signal processor may process signals such as to provide for a specified hearing device functionality. The signal processor may process signals such as to compensate for the user's hearing loss or hearing impairment, such compensation may involve frequency dependent amplification of the input signal based on the user's hearing loss. The signal processor may provide a modified signal. The signal processor may process signals such as to provide Tinnitus masking. The signal processor may process signals such as to provide for streaming of audio signals.

The hearing device comprises an output transducer for providing an audio output signal based on an output signal from the signal processor. The output transducer is coupled to an output of the signal processer for conversion of an output signal from the signal processor into an audio output signal. Examples of the output transducer are receivers, such as a speaker, for generating an audio output signal or a cochlear implant for generating an electric stimulus signal to the auditory nerve of the user.

The hearing device may be a headset, a hearing aid, a hearable etc. The hearing device may be an in-the-ear (ITE) hearing device, a receiver-in-ear (RIE) hearing device, a receiver-in-canal (RIC) hearing device, a microphone-and-receiver-in-ear (MaRIE) hearing device, a behind-the-ear (BTE) hearing device, an over-the-counter (OTC) hearing device etc, a one-size-fits-all hearing device etc.

The hearing device is configured to be worn by a user. The hearing device may be arranged at the user's ear, on the user's ear, in the user's ear, in the user's ear canal, behind the user's ear etc. The user may wear two hearing devices, one hearing device at each ear. The two hearing devices may be connected, such as wirelessly connected.

The hearing device may be configured for audio communication, e.g. enabling the user to listen to media, such as music or radio, and/or enabling the user to perform phone calls. The hearing device may be configured for performing hearing compensation for the user. The hearing device may be configured for performing noise cancellation etc.

The hearing device may comprise a first input transducer, e.g. a microphone, to generate one or more microphone output signals based on a received audio signal. The audio signal may be an analogue signal. The microphone output signal may be a digital signal. Thus, the first input transducer, e.g. microphone, or an analogue-to-digital converter, may convert the analogue audio signal into a digital microphone output signal. All the signals may be sound signals or signals comprising information about sound. The hearing device may comprise a signal processor. The one or more microphone output signals may be provided to the signal processor for processing the one or more microphone output signals. The signals may be processed such as to compensate for a user's hearing loss or hearing impairment. The signal processor may provide a modified signal. All these components may be comprised in a housing of an ITE unit or a BTE unit. The hearing device may comprise a receiver or output transducer or speaker or loudspeaker. The receiver may be connected to an output of the signal processor. The receiver may output the modified signal into the user's ear. The receiver, or a digital-to-analogue converter, may convert the modified signal, which is a digital signal, from the processor to an analogue signal. The receiver may be comprised in an ITE unit or in an earpiece, e.g. RIE unit or MaRIE unit. The hearing device may comprise more than one microphone, and the ITE unit or BTE unit may comprise at least one microphone and the RIE unit may also comprise at least one microphone.

The hearing device signal processor may comprise elements such as an amplifier, a compressor and/or a noise reduction system etc. The signal processor may be implemented in a signal-processing chip or a printed circuit board (PCB). The hearing device may further have a filter function, such as compensation filter for optimizing the output signal.

The hearing device may furthermore comprise a wireless communication unit or chip, such as a wireless communication circuit or a magnetic induction chip, for wireless data communication interconnected with an antenna, such as an radio frequency (RF) antenna or a magnetic induction antenna, for emission and reception of an electromagnetic field. The wireless communication unit including a radio or a transceiver, may connect to the hearing device signal processor and the antenna, for communicating with one or more external devices, such as one or more external electronic devices, including at least one smart phone, at least one tablet, at least one hearing accessory device, including at least one spouse microphone, remote control, audio testing device, etc., or, in some embodiments, with another hearing device, such as another hearing device located at another ear, typically in a binaural hearing device system.

The hearing device may be any hearing device, such as any hearing device compensating a hearing loss of a wearer of the hearing device, or such as any hearing device providing sound to a wearer, or such as a hearing device providing noise cancellation, or such as a hearing device providing tinnitus reduction/masking. The person skilled in the art is well aware of different kinds of hearing devices and of different options for arranging the hearing device in and/or at the ear of the hearing device wearer.

For example, the hearing device may be an In-The-Ear (ITE), Receiver-In-Canal (RIC) or Receiver-In-the-Ear (RIE or RITE) or a Microphone-and-Receiver-In-the-Ear (MaRIE) type hearing device, in which a receiver is positioned in the ear, such as in the ear canal, of a wearer during use, for example as part of an in-the-ear unit, while other hearing device components, such as a processor, a wireless communication unit, a battery, etc. are provided as an assembly and mounted in a housing of a Behind-The-Ear (BTE) unit. A plug and socket connector may connect the BTE unit and the earpiece, e.g. RIE unit or MaRIE unit.

The hearing device may comprise a RIE unit. The RIE unit typically comprises the earpiece such as a housing, a plug connector, and an electrical wire/tube connecting the plug connector and earpiece. The earpiece may comprise an in-the-ear housing, a receiver, such as a receiver configured for being provided in an ear of a user and/or a receiver being configured for being provided in an ear canal of a user, and an open or closed dome. The dome may support correct placement of the earpiece in the ear of the user. The RIE unit may comprise a microphone, a receiver, one or more sensors, and/or other electronics. Some electronic components may be placed in the earpiece, while other electronic components may be placed in the plug connector. The receiver may be with a different strength, i.e. low power, medium power, or high power. The electrical wire/tube provides an electrical connection between electronic components provided in the earpiece of the RIE unit and electronic components provided in the BTE unit. The electrical wire/tube as well as the RIE unit itself may have different lengths.

The hearing device may comprise a power source, such as a replaceable battery or a rechargeable battery. The hearing device may comprise a power management unit. The power management unit may be provided for controlling the power provided from the power source to the signal processor, the output transducer, the input transducer, and the transceiver. Furthermore, the hearing device may comprise a housing or a shell. The power source and the power management unit of the hearing device may be arranged in the housing, e.g. in a compartment or in a frame in the housing.

In some embodiments, the time monitor is configured to detect that the expiry time of the subscription is reached by comparing elapsed time with a predefined threshold. The predefined threshold may be a date, a period of time, a count etc. The comparison of elapsed time may be performed regularly, such as every month, every week, every day, every hour, every minute, etc.

In some embodiments, the time monitor is connected to the signal processor, whereby the processing of the input signals is configured to be stopped or altered, if the expiry time of the subscription is reached. Thus, the time monitor may send a signal/command to the signal processor with information to either stop or alter the signal processing, when the time monitor detects that the expiry time of the subscription is reached.

In some embodiments, the hearing device continues the processing of the input signals, if the subscription is renewed before the expiry time is reached. Thus if the expiry time is not reached because the subscription is renewed before the subscription expires, then the hearing device continues to operate as normally, i.e. according to the functionality and specification which is paid for.

In some embodiments, the time monitor is configured to automatically and/or autonomously monitor time.

In some embodiments, the time monitor is a software component in the hearing device. In some embodiments the time monitor is one or more of:
 a calendar;
 a time meter/counter for measuring a period of time;
 an event counter for counting a number of predetermined event occurrences.

If the time monitor is a calendar, then there be a setting of a date some days/weeks/months/years ahead of time. In this case, the actual date and an end date may be compared for detecting when the expiry time is reached.

If the time monitor is a time meter/counter, then there be a count of hours/days/months/year since the last subscription payment, or a count of total hours of use/on-time of the hearing device. In this case, the actual counted time may be compared with a threshold time for detecting when the expiry time is reached.

If the time monitor is an event counter, then there may be a counting of a number of predetermined event occurrences. The events may be number of battery recharging and/or number of battery changes, and/or number of on/off switches of the hearing device. In this case, the actual counted events may be compared with a threshold event count for detecting when the expiry time is reached.

In some embodiments, the hearing device comprises:
 an antenna for emission and reception of an electromagnetic field,
 a transceiver coupled to the signal processor and to the antenna, the transceiver is configured for wireless data communication with an associated electronic device.

The hearing device comprises a transceiver. The transceiver is coupled to the signal processor. The transceiver is configured for wireless data communication. The transceiver is configured for communication with a connected electronic device e.g. a smartphone, tablet, pc etc. Examples of transceivers are a radio or wireless communication unit and a transmitter/receiver pair (T/R).

The hearing device comprises an antenna for emission and reception of an electromagnetic field. The antenna is coupled to the transceiver. The antenna is configured for communication with a connected device e.g. a smartphone.

The transceiver may comprise one or more wireless communication units. The transceiver is interconnected with the antenna for emission and reception of an electromagnetic field. The wireless communication unit may comprise a transmitter, a receiver, a transmitter/receiver pair, such as a transceiver, a radio, a radio circuit, etc. The wireless communication unit may be configured for communication using any protocol as known for a person skilled in the art, including Bluetooth, including Bluetooth Low Energy, Bluetooth Smart, etc., WLAN standards, manufacture specific protocols, such as tailored proximity antenna protocols, such as proprietary protocols, such as low-power wireless communication protocols, such as CSR mesh, etc.

The hearing device may be connected to a plethora of electronic devices or accessories, that can be either body-worn or placed in the user's proximity, and hence to the internet as part of the so-called internet of things (IoT). The 2.4 GHz ISM band may be preferred due to the presence of many harmonized standards for low-power communications, such as BLE or ZigBee, its worldwide availability for industrial use, and the trade-off between power consumption and range that can be achieved. Thus, the 2.4 GHz band may be used for hearing device communication.

In some embodiments, the action which the hearing device is configured to perform when the expiry time of the subscription is reached is one or more of:
 connecting with a computer program product on an associated electronic device;
 providing a notification that the expiry time of the subscription is reached;
 entering into a predefined mode.

The hearing device may connect with a computer program product, e.g. a software application or "app", on an associated electronic device, e.g. the user's smartphone, for checking if the subscription has been renewed or paid, and if it has, then the hearing device may continue to operate and function as normally or the hearing device may receive an active feature set for the hearing device such that the hearing device can continue to operate and function as normally.

The hearing device may provide a notification that the expiry time of the subscription is reached. The notification can be an alert to the user, such as an audio alert, e.g. a voice prompt saying "subscription must be renewed" or e.g. a "beep" sound in hearing device output transducer, which notifies the user and which may be annoying for the user, thereby encouraging the user to renew the subscription. The notification can be an alert to the user, such as a visual alert, e.g. a blinking light, for example on the surface of the hearing device.

In some embodiments, the predefined mode, which the hearing device is configured to enter into, comprises one or more of:
the hearing device stops operating;
the hearing device outputs an audio alert;
the hearing device uses/applies predefined settings for the hearing device functionality.

The predefined mode is the mode which the hearing device may enter into when the expiry time of the subscription is reached. In the predefined mode, the hearing device may stop operating, i.e. the hearing device may shut down or may provide no signal processing of the input signals. In the predefined mode, the hearing device may output an audio alert, such as a periodic or constant audio alert. In the predefined mode, the hearing device may use or apply predefined settings for the hearing device functionality. The hearing device functionality may comprise both hearing compensation, Tinnitus masking or other functionalities of a hearing device, e.g. streaming of audio. The predefined settings for the hearing device functionality may comprise a limited functionality such as a downgrade.

In some embodiments, the hearing device functionality comprises one or more of:
hearing loss compensation;
Tinnitus masking;
streaming of audio.

The hearing device functionality may be adjusted or controlled by adjusting gain, adjusting frequency ranges, changing modes etc. Streaming of audio may e.g. be music, sound and/or voice from a phone call, and e.g. be from an associated electronic device.

In some embodiments, upon connecting with a computer program product on the associated electronic device, the hearing device is configured to receive a new expiry time of the subscription and an active feature set transmitted via the computer program product from the subscription server. The hearing device is configured to receive a new expiry time of the subscription, for example when the subscription is renewed or paid. The hearing device is configured to receive an active feature set for the signal processing of input sounds. The active feature set is configured to be transmitted to the hearing device via the computer program product from the subscription server. The active feature set may be a renewal or an upgrade of the hearing device functionality.

In some embodiments, the active feature set comprises one or more parameters and/or algorithms provided to the signal processor of the hearing device for specifying the hearing device functionality.

According to an aspect, disclosed is a system comprising:
a hearing device configured to be arranged at a user's ear,
a computer program product provided in an electronic device associated with the hearing device;
a subscription server configured for communication with the computer program product;
where the hearing device comprises:
an input transducer for generating one or more input signals based on a received audio signal;
a signal processor configured for processing the one or more input signals;
an output transducer for providing an audio output signal based on an output signal from the signal processor;
wherein the hearing device comprises a time monitor for monitoring an expiry time of a subscription for the hearing device provided by a subscription server,
wherein the hearing device is configured to perform an action when the time monitor detects that the expiry time of the subscription is reached;
wherein the hearing device is configured to connect to the computer program product;
wherein the computer program product is configured to connect to the subscription server for checking the subscription status of the hearing device.

The subscription status of the hearing device can be for example: new subscription is payed/renewed, or new subscription is not yet payed/renewed.

In some embodiments, the subscription server is configured to transmit an active feature set to the computer program product; and wherein the computer program product is configured to transmit the active feature set to the hearing device.

The subscription server may be configured to transmit an active feature set to the computer program product when the subscription is paid/renewed. The subscription server may also be configured to transmit a new expiry date of the subscription to the computer program product.

If the subscription is not paid/renewed, then e.g. the feature set may remain the same in the hearing device, and/or the feature set may be turned off or be inactive.

According to an aspect, disclosed is a subscription server configured for providing a subscription service for a subscription of a hearing device configured to be worn by a user, where the subscription service comprises periodic subscription payment to be paid by the user, the subscription server being configured for communication with a computer program product on an electronic device associated with the hearing device, and where the subscription server is configured for transmission of an active feature set to the hearing device via the computer program product as part of the subscription service.

The subscription server may be a cloud server, a remote server etc. The subscription server may be owned and controlled by the hearing device manufacturer. The subscription server and system may be operated by the hearing device manufacturer. The hearing care providers (HCPs) may have access to the system and/or to the subscription server to service their particular customers, i.e. the hearing device users.

The subscription service comprises periodic subscription payment to be paid by the user, e.g. via the computer program product, i.e. a hearing device "app", or via another electronic payment method, such as Apple pay, or Danish Mobilepay or other credit card transactions.

According to an aspect, disclosed is a computer program product provided on an electronic device, the electronic device being associated with a hearing device configured to be worn by a user, the computer program product is configured to connect to a subscription server for checking the subscription status of the hearing device, the computer program product is configured to receive an active feature set from the subscription server, the computer program product is configured to connect to the hearing device and to transmit the active feature set to the hearing device.

The subscription status of the hearing device can be for example: new subscription is payed/renewed, or new subscription is not yet payed/renewed.

The subscription server may be configured to transmit an active feature set to the computer program product when the subscription is paid/renewed. The subscription server may also be configured to transmit a new expiry date of the subscription to the computer program product.

If the subscription is not paid/renewed, then e.g. the feature set may remain the same in the hearing device, and/or the feature set may be turned off or be inactive.

In some embodiments, the computer program product is a hearing device app and/or a payment app.

Thus, the subscription service comprises periodic subscription payment to be paid by the user, e.g. via the computer program product, i.e. a hearing device "app", or via another electronic payment method, such as Apple pay, or Danish Mobilepay or other credit card transactions.

According to an aspect, disclosed is a method in a hearing device, the method comprising:
monitoring, by a time monitor in the hearing device, an expiry time of a subscription for the hearing device provided by a subscription server;
performing an action, by the hearing device, when the time monitor detects that the expiry time of the subscription is reached.

According to an aspect, disclosed is a method in a system, the system comprising:
a hearing device configured to be arranged at a user's ear,
a computer program product provided in an electronic device associated with the hearing device;
a subscription server configured for communication with the computer program product;
the method comprising:
monitoring, by a time monitor in the hearing device, an expiry time of a subscription for the hearing device provided by a subscription server,
performing an action, by the hearing device, when the time monitor detects that the expiry time of the subscription is reached;
connecting the hearing device to the computer program product;
connecting the computer program product to the subscription server for checking the subscription status of the hearing device.

The subscription status of the hearing device can be for example: new subscription is payed/renewed, or new subscription is not yet payed/renewed.

In some embodiments, the method further comprises:
transmitting an active feature set from the subscription server to the computer program product; and
transmitting the active feature set from the computer program product to the hearing device.

The subscription server may be configured to transmit an active feature set to the computer program product when the subscription is paid/renewed. The subscription server may also be configured to transmit a new expiry date of the subscription to the computer program product.

If the subscription is not paid/renewed, then e.g. the feature set may remain the same in the hearing device, and/or the feature set may be turned off or be inactive.

According to an aspect, disclosed is a computer program product comprising instructions which, when the program is executed by a computer, cause the computer to carry out the method disclosed above.

According to an aspect, disclosed is a method in a system. The method comprises checking if the expiry time is reached. If the expiry time is not reached, the method repeats the step of checking if the expiry is reached. If the expiry time is reached, then the method continues to check if the subscription is renewed. If the subscription is renewed, the method returns to the step of checking if the expiry time is reached. If the subscription is not renewed, the method continues to a step where the hearing device performs an action. After the hearing device has performed an action, the method continues by returning to the step of checking if the subscription is renewed.

The present disclosure relates to different aspects including the hearing device described above and in the following, and corresponding systems, subscription servers, computer product products, methods, devices, uses and/or product means, each yielding one or more of the benefits and advantages described in connection with the first mentioned aspect, and each having one or more embodiments corresponding to the embodiments described in connection with the first mentioned aspect and/or disclosed in the appended claims.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout, the same reference numerals are used for identical or corresponding parts.

Figure 1:
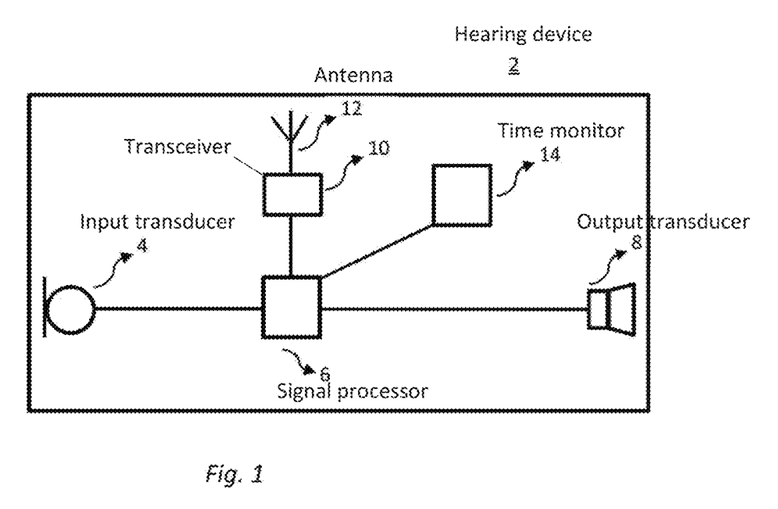
FIG. 1 schematically illustrates an example of a hearing device.

FIG. 1 schematically illustrates an example of a hearing device 2 configured to be arranged at a user's ear. The hearing device 2 comprises an input transducer 4 for generating one or more input signals based on a received audio signal. The hearing device 2 comprises a signal processor 6 configured for processing the one or more input signals. The hearing device 2 comprises an output transducer 8 for providing an audio output signal based on an output signal from the signal processor 6. The hearing device 2 comprises a time monitor 14 for monitoring an expiry time of a subscription for the hearing device 2 provided by a subscription server. The hearing device 2 is configured to perform an action when the time monitor 14 detects that the expiry time of the subscription is reached.

The hearing device 2 may continue the processing of the input signals, if the subscription is renewed before the expiry time is reached.

The hearing device 2 may comprise an antenna 12 for emission and reception of an electromagnetic field. The hearing device 2 may comprise a transceiver 10 coupled to the signal processor 6 and to the antenna 12. The transceiver 10 is configured for wireless data communication with an associated electronic device.

The time monitor 14 is configured to detect that the expiry time of the subscription is reached by comparing elapsed time with a predefined threshold.

The time monitor 14 is connected to the signal processor 6, whereby the processing of the input signals is configured to be stopped or altered, if the expiry time of the subscription is reached.

The time monitor 14 may be a software component in the hearing device 2. The time monitor 14 may be one or more of a calendar; a time meter/counter for measuring a period of time; and/or an event counter for counting a number of predetermined event occurrences.

The action which the hearing device 2 is configured to perform when the expiry time of the subscription is reached may be one or more of: connecting with a computer program product on an associated electronic device; providing a notification that the expiry time of the subscription is reached; and/or entering into a predefined mode.

The predefined mode, which the hearing device 2 is configured to enter into, may comprise one or more of: the hearing device 2 stops operating; the hearing device 2 outputs an audio alert; and/or the hearing device 2 uses/applies predefined settings for the hearing device functionality.

The hearing device functionality may comprise one or more of: hearing loss compensation; Tinnitus masking; and/or streaming of audio.

The haring device 2 is configured to connect with a computer program product on an associated electronic device. Upon connecting with a computer program product on the associated electronic device, the hearing device 2 is configured to receive a new expiry time of the subscription and an active feature set transmitted via the computer program product from the subscription server. The active feature set may comprise one or more parameters/algorithms provided to the signal processor 6 of the hearing device 2 for specifying the hearing device functionality.

Figure 2:
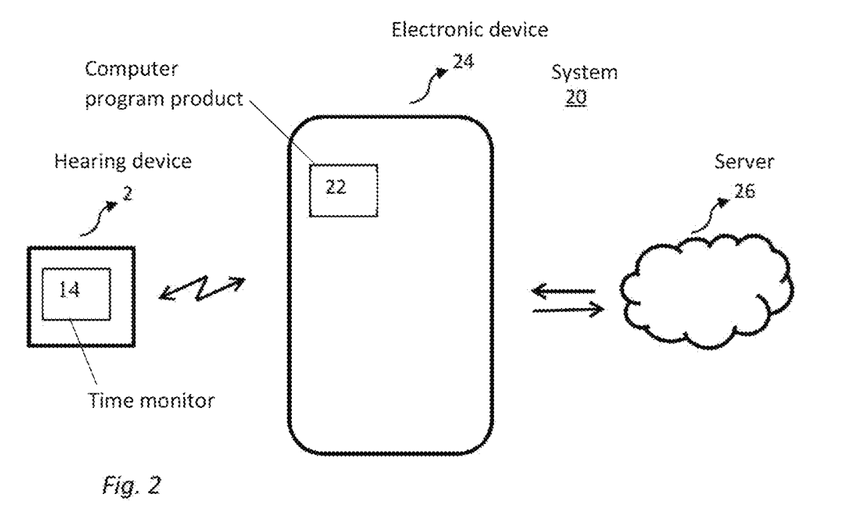
FIG. 2 schematically illustrates an example of a system comprising a hearing device, a computer program product provided in an electronic device, and a subscription server.

FIG. 2 schematically illustrates an example of a system 20. The system 20 comprises a hearing device 2 configured to be arranged at a user's ear. The system 20 comprises a computer program product 22 provided in an electronic device 24 associated with the hearing device 2. The system 20 comprises a subscription server 26 configured for communication with the computer program product 22. The hearing device 2 may comprise, see FIG. 1: an input transducer for generating one or more input signals based on a received audio signal; a signal processor configured for processing the one or more input signals; an output transducer for providing an audio output signal based on an output signal from the signal processor. The hearing device 2 comprises a time monitor 14 for monitoring an expiry time of a subscription for the hearing device 2 provided by the subscription server 26.

The hearing device 2 is configured to perform an action when the time monitor 14 detects that the expiry time of the subscription is reached. The action which the hearing device 2 is configured to perform when the expiry time of the subscription is reached may be one or more of: connecting with the computer program product 22 on the associated electronic device 24; providing a notification that the expiry time of the subscription is reached; and/or entering into a predefined mode.

If the hearing device 2 has connected to the computer program product 22; the computer program product 22 may connect to the subscription server 26 for checking the subscription status of the hearing device 2.

The subscription server 26 is configured to transmit an active feature set to the computer program product 22; and the computer program product 22 is configured to transmit the active feature set to the hearing device 2.

The subscription server 26 is configured for providing a subscription service for a subscription of the hearing device 2 configured to be worn by a user. The subscription service comprises periodic subscription payment to be paid by the user. The subscription server 26 is configured for communication with a computer program product 22 on an electronic device 24 associated with the hearing device 2. The subscription server 26 is configured for transmission of an active feature set to the hearing device 2 via the computer program product 22 as part of the subscription service.

The computer program product 22 is provided on an electronic device 24. The electronic device 24 is associated with a hearing device 2 configured to be worn by a user. The computer program product 22 is configured to connect to a subscription server 26 for checking the subscription status of the hearing device 2. The computer program product 22 is configured to receive an active feature set from the subscription server 26. The computer program product 22 is configured to connect to the hearing device 2 and to transmit the active feature set to the hearing device 2.

The computer program product 22 may be a hearing device app and/or a payment app.

Figure 3A:
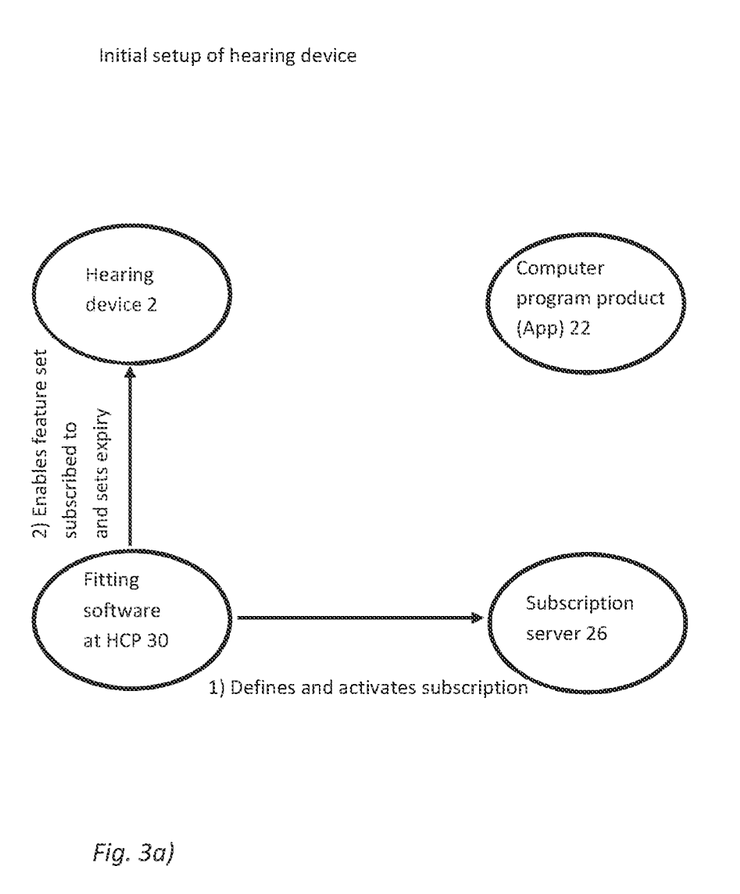
FIGS. 3*a*, 3*b* and 3*c* schematically illustrate examples of the connections and transmissions between the hearing device, the computer program product, the subscription server and the fitting software at the hearing care professional (HCP).
Figure 3B:
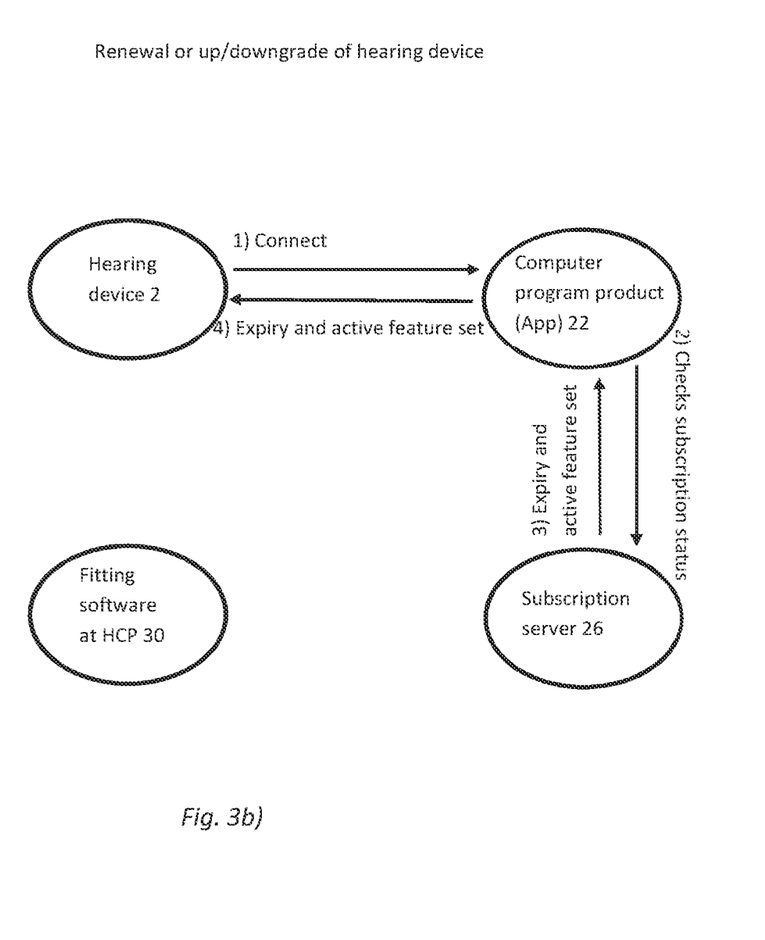
Figure 3C:
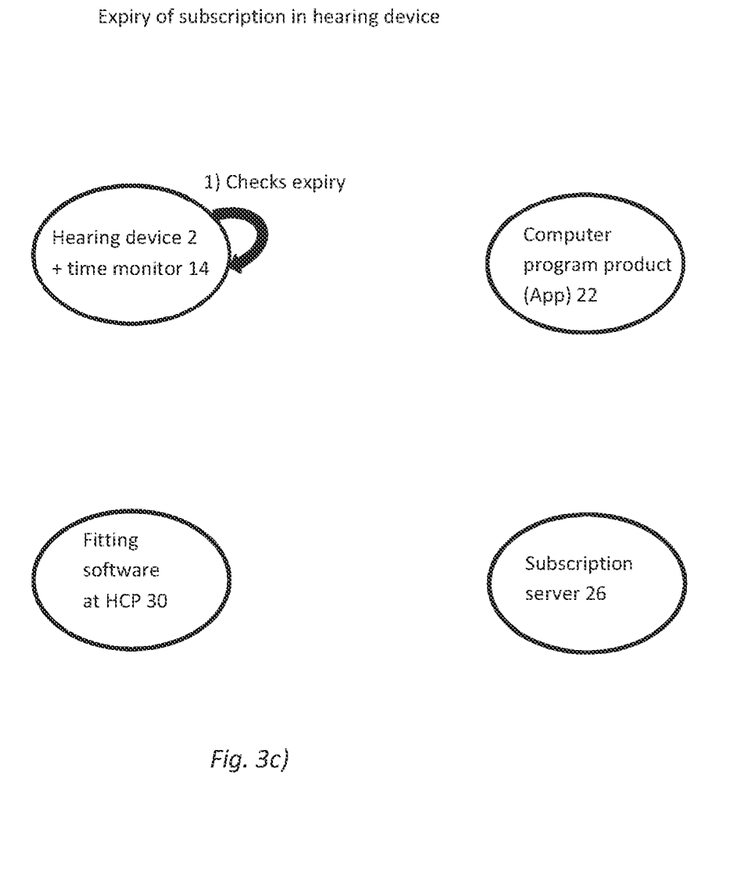

FIGS. 3*a*, 3*b* and 3*c* schematically illustrate examples of the connections and transmissions between the hearing device 2, the computer program product 22, the subscription server 26 and the fitting software at the hearing care professional (HCP) 30.

FIG. 3*a* schematically illustrates an example of the initial setup of a hearing device 2. The fitting software at the hearing care professional (HCP) 30 defines and activates the subscription, and this is transmitted (step 1) from the fitting software at the hearing care professional (HCP) 30 to the subscription server 26. Then the fitting software at the hearing care professional (HCP) 30 enables a feature set subscribed to and sets an expiry, and this is transmitted (step 2) to the hearing device 2.

Now the hearing device 2 is set up for the user.

FIG. 3*b* schematically illustrates an example of a renewal or up/downgrade of hearing device 2. The hearing 2 connects (step 1) with the computer program product 22. The computer program product 22 checks (step 2) the subscription status by connecting to the subscription server 26. The subscription server 26 transmits (step 3) an expiry and active feature set to the computer program product 22. The computer program product 22 transmits (step 4) the expiry and active feature set to the hearing device 2.

Now the hearing device 2 is renewed or up/downgraded with a (new) active feature set.

The connections and transmissions in this FIG. 3b may be performed as long as the expiry time of the subscription is not reached yet.

FIG. 3c schematically illustrates an example of checking the expiry of subscription in the hearing device 2. The hearing device 2 checks (step 1) expiry of the subscription by itself. The hearing device 2 comprises a time monitor 14 for monitoring the expiry time of the subscription for the hearing device 2 provided by a subscription server 26. The time monitor 14 detects when the expiry time of the subscription is reached.

Figure 4A:
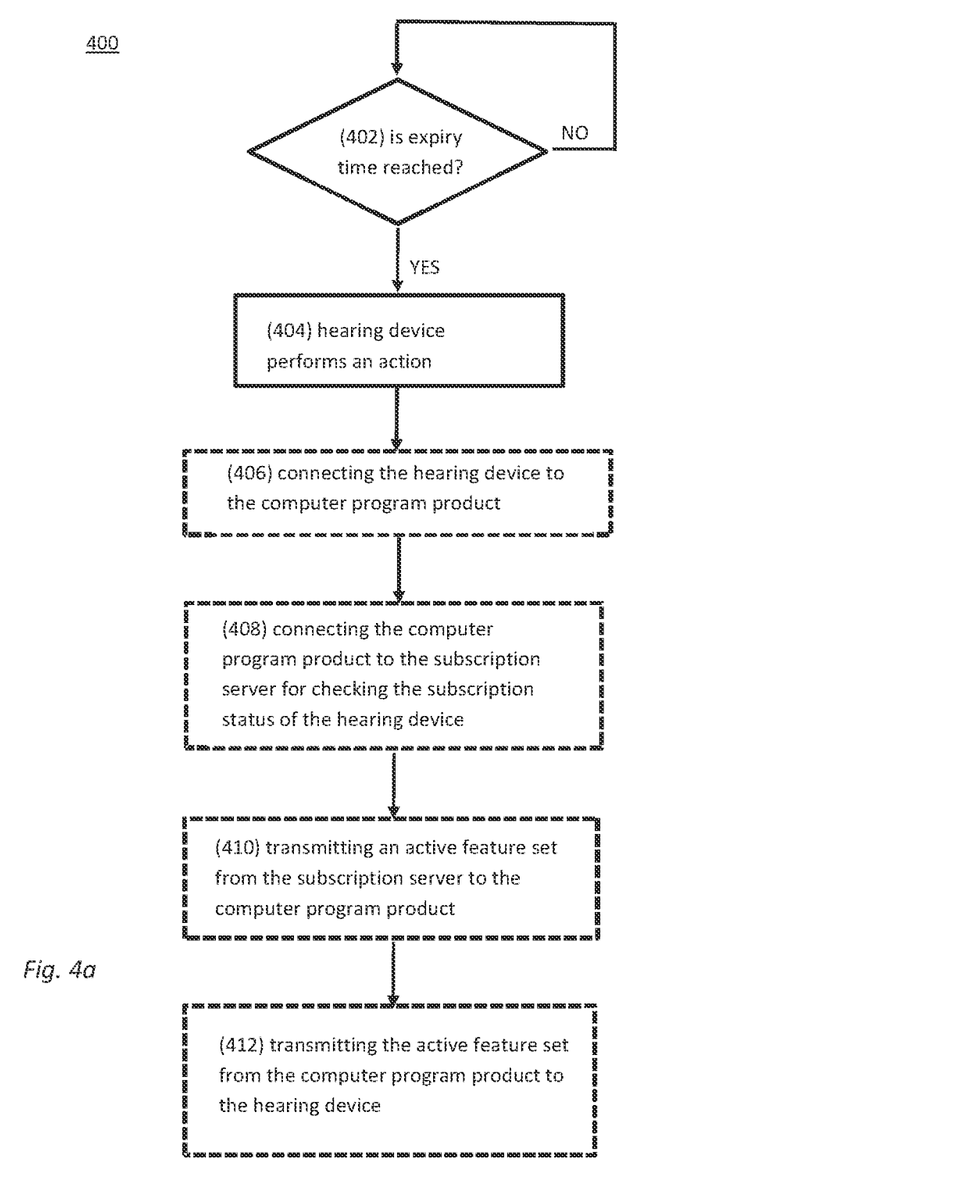
FIGS. 4*a* and 4*b* schematically illustrate examples of a method in a system.
Figure 4B:
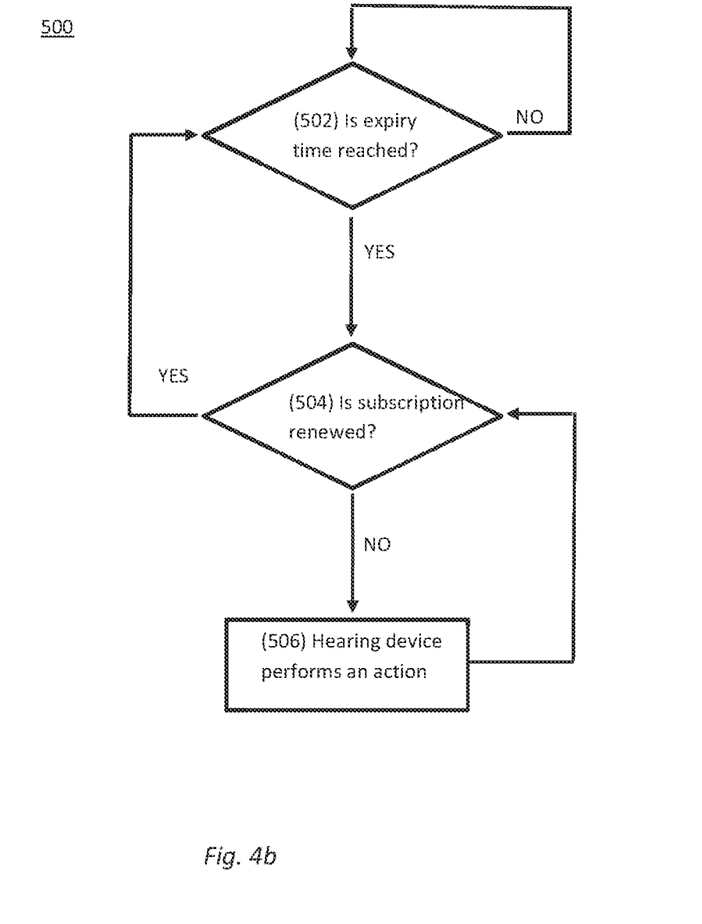

FIGS. 4a and 4b schematically illustrate examples of a method 400, 500 in a system.

The system 20 may be as shown in FIG. 2 or in FIGS. 3a, 3b and 3c. The system 20 comprises a hearing device 2 configured to be arranged at a user's ear. The system 20 comprises a computer program product 22 provided in an electronic device 24 associated with the hearing device 2. The system 20 comprises a subscription server 26 configured for communication with the computer program product 22.

In FIG. 4a), the method 400 comprises, in step 402, monitoring, by a time monitor 14 in the hearing device 2, an expiry time of a subscription for the hearing device 2 provided by a subscription server 26. The monitoring is performed by, in step 402, that the method comprises checking if the expiry time is reached.

The method comprises, in step 404, performing an action, by the hearing device 2, when the time monitor 14 detects that the expiry time of the subscription is reached.

The method may comprise that the performed action comprises, in step 406, connecting the hearing device 2 to the computer program product 22.

The method may comprise, in step 408, connecting the computer program product 22 to the subscription server 26 for checking the subscription status of the hearing device 2.

The method may comprise, in step 410, transmitting an active feature set from the subscription server 26 to the computer program product 22.

The method may comprise, in step 412, transmitting the active feature set from the computer program product to the hearing device.

In FIG. 4b), the method 500 comprises, in step 502, checking if the expiry time is reached. If the expiry time is not reached, the method repeats step 502 of checking if the expiry is reached.

If the expiry time is reached, then the method continues to step 504, for checking if the subscription is renewed. If the subscription is renewed, the method returns to step 502 for checking if the expiry time is reached.

If the subscription is not renewed, the method continues to step 506 where the hearing device performs an action.

After the hearing device has performed an action in step 506, the method continues by returning to step 504 for checking if the subscription is renewed.

Although particular features have been shown and described, it will be understood that they are not intended to limit the claimed invention, and it will be made obvious to those skilled in the art that various changes and modifications may be made without departing from the scope of the claimed invention. The specification and drawings are, accordingly to be regarded in an illustrative rather than restrictive sense. The claimed invention is intended to cover all alternatives, modifications and equivalents.

Items

1. A hearing device (2) configured to be arranged at a user's ear, the hearing device (2) comprising:
   an input transducer (4) for generating one or more input signals based on a received audio signal;
   a signal processor (6) configured for processing the one or more input signals;
   an output transducer (8) for providing an audio output signal based on an output signal from the signal processor (6);
   wherein the hearing device (2) comprises a time monitor (14) for monitoring an expiry time of a subscription for the hearing device (2) provided by a subscription server,
   wherein the hearing device is configured to perform an action when the time monitor detects that the expiry time of the subscription is reached.
2. The hearing device according to any of the preceding items, wherein the time monitor (14) is configured to detect that the expiry time of the subscription is reached by comparing elapsed time with a predefined threshold.
3. The hearing device according to any of the preceding items, wherein the time monitor is connected to the signal processor, whereby the processing of the input signals is configured to be stopped or altered, if the expiry time of the subscription is reached.
4. The hearing device according to any of the preceding items, wherein the hearing device continues the processing of the input signals, if the subscription is renewed before the expiry time is reached.
5. The hearing device according to any of the preceding items, wherein the time monitor (14) is configured to automatically/autonomously monitor time.
6. The hearing device according to any of the preceding items, wherein the time monitor is a software component in the hearing device, and wherein the time monitor is one or more of:
   a calendar;
   a time meter/counter for measuring a period of time;
   an event counter for counting a number of predetermined event occurrences.
7. The hearing device according to any of the preceding items, wherein the hearing device comprises:
   an antenna (12) for emission and reception of an electromagnetic field,
   a transceiver (10) coupled to the signal processor (6) and to the antenna (12), the transceiver (10) is configured for wireless data communication with an associated electronic device.
8. The hearing device according to any of the preceding items, wherein the action which the hearing device is configured to perform when the expiry time of the subscription is reached is one or more of:
   connecting with a computer program product on an associated electronic device;
   providing a notification that the expiry time of the subscription is reached;
   entering into a predefined mode.
9. The hearing device according to the preceding item, wherein the predefined mode, which the hearing device is configured to enter into, comprises one or more of:
   the hearing device stops operating;
   the hearing device outputs an audio alert;

the hearing device uses/applies predefined settings for the hearing device functionality.
10. The hearing device according to the preceding item, wherein the hearing device functionality comprises one or more of:
hearing loss compensation;
Tinnitus masking;
streaming of audio.
11. The hearing device according to any of the preceding items, wherein upon connecting with a computer program product on the associated electronic device, the hearing device is configured to receive a new expiry time of the subscription and an active feature set transmitted via the computer program product from the subscription server.
12. The hearing device according to the preceding item, wherein the active feature set comprises one or more parameters/algorithms provided to the signal processor of the hearing device for specifying the hearing device functionality.
13. A system comprising:
a hearing device (2) configured to be arranged at a user's ear,
a computer program product provided in an electronic device associated with the hearing device;
a subscription server configured for communication with the computer program product;
where the hearing device (2) comprises:
an input transducer (4) for generating one or more input signals based on a received audio signal;
a signal processor (6) configured for processing the one or more input signals;
an output transducer (8) for providing an audio output signal based on an output signal from the signal processor (6);
wherein the hearing device (2) comprises a time monitor (14) for monitoring an expiry time of a subscription for the hearing device (2) provided by a subscription server,
wherein the hearing device is configured to perform an action when the time monitor detects that the expiry time of the subscription is reached;
wherein the hearing device is configured to connect to the computer program product;
wherein the computer program product is configured to connect to the subscription server for checking the subscription status of the hearing device.
14. The system according to the preceding item, wherein the subscription server is configured to transmit an active feature set to the computer program product; and
wherein the computer program product is configured to transmit the active feature set to the hearing device.
15. A subscription server configured for providing a subscription service for a subscription of a hearing device configured to be worn by a user, where the subscription service comprises periodic subscription payment to be paid by the user, the subscription server being configured for communication with a computer program product on an electronic device associated with the hearing device, and where the subscription server is configured for transmission of an active feature set to the hearing device via the computer program product as part of the subscription service.
16. A computer program product provided on an electronic device, the electronic device being associated with a hearing device configured to be worn by a user, the computer program product is configured to connect to a subscription server for checking the subscription status of the hearing device, the computer program product is configured to receive an active feature set from the subscription server, the computer program product is configured to connect to the hearing device and to transmit the active feature set to the hearing device.
17. A computer program product according to the preceding item, wherein the computer program product is a hearing device app and/or a payment app.
18. A method in a hearing device, the method comprising:
monitoring, by a time monitor (14) in the hearing device, an expiry time of a subscription for the hearing device (2) provided by a subscription server;
performing an action, by the hearing device, when the time monitor (14) detects that the expiry time of the subscription is reached.
19. A method in a system, the system comprising:
a hearing device (2) configured to be arranged at a user's ear,
a computer program product provided in an electronic device associated with the hearing device;
a subscription server configured for communication with the computer program product;
the method comprising:
monitoring, by a time monitor (14) in the hearing device, an expiry time of a subscription for the hearing device (2) provided by a subscription server,
performing an action, by the hearing device (2), when the time monitor (14) detects that the expiry time of the subscription is reached;
connecting the hearing device (2) to the computer program product;
connecting the computer program product to the subscription server for checking the subscription status of the hearing device (2).
20. The method in the system according to the preceding item, further comprising:
transmitting an active feature set from the subscription server to the computer program product; and
transmitting the active feature set from the computer program product to the hearing device (2).

LIST OF REFERENCES 2 hearing device
4 input transducer
6 signal processor
8 output transducer
10 transceiver
12 antenna
14 time monitor
20 system
22 computer program product
24 electronic device
26 subscription server
30 fitting software at hearing care professional (HCP)
400 method
402 method step of monitoring, by a time monitor in the hearing device, an expiry time of a subscription for the hearing device
404 method step of performing an action, by the hearing device, when the time monitor detects that the expiry time of the subscription is reached
406 method step of connecting the hearing device to the computer program product 408 method step of connecting the computer program product to the subscription server for checking the subscription status of the hearing device 410 method step of transmitting an active feature set from the subscription server to the computer program product 412 method step of transmitting the active feature set from the computer program product to the hearing device 500 method 502 method step of checking if the expiry time is reached 504 method step of checking if the subscription is renewed 506 method step where the hearing device performs an action

The invention claimed is:

1. A hearing device configured to be arranged at an ear of a user, the hearing device comprising:
   an input transducer configured to generate one or more input signals based on a received audio signal;
   a signal processor configured to provide an output signal based on the one or more input signals;
   an output transducer configured to provide an audio output signal based on the output signal from the signal processor; and
   a time monitor configured to monitor an expiry time of a subscription for the hearing device;
   wherein the hearing device is configured to perform an action when the time monitor detects that the expiry time of the subscription is reached; and
   wherein the action which the hearing device is configured to perform when the expiry time of the subscription is reached is one or more of:
      connecting with a program product in an electronic device;
      providing a notification that the expiry time of the subscription is reached; or
      entering into a predefined mode.

2. The hearing device according to claim 1, wherein the time monitor is configured to detect that the expiry time of the subscription is reached by comparing an elapsed time with a threshold.

3. The hearing device according to claim 1, wherein the time monitor is a software component in the hearing device.

4. The hearing device according to claim 1, wherein the time monitor is one or more of:
   a calendar;
   a time meter/counter for measuring a period of time; or
   an event counter.

5. The hearing device according to claim 1, wherein the hearing device is configured to enter into the mode as the action, and wherein when the hearing device is in the mode, the hearing device is configured to:
   stop operating;
   output an audio alert;
   use or apply a predefined setting; or
   any combination of the foregoing.

6. The hearing device according to claim 1, wherein the hearing device is configured to connect with the program product as the action.

7. The hearing device according to claim 6, wherein the hearing device is configured to receive a new expiry time of the subscription via the program product.

8. The hearing device according to claim 1, wherein the hearing device is configured to receive information regarding a feature of the hearing device via the program product in the electronic device of the user.

9. The hearing device according to claim 8, wherein the information is associated with a renewal or an upgrade of a functionality of the hearing device.

10. The hearing device according to claim 8, wherein the information comprises one or more parameters and/or algorithms for specifying and/or implementing a functionality for the hearing device.

11. The hearing device according to claim 1, wherein the expiry time is provided by a server.

12. A system comprising the hearing device of claim 1, and the electronic device, wherein the hearing device is configured to connect to the program product in the electronic device, and wherein the program product is configured to connect to a server for checking a subscription status of the hearing device.

13. The system of claim 12, further comprising the server, wherein the server is configured to communicate with the program product in the electronic device of the user.

14. A system comprising the hearing device of claim 1, and a server, wherein the server is configured to provide a new expiry time for reception by the hearing device.

15. A hearing device configured to be arranged at an ear of a user, the hearing device comprising:
   an input transducer configured to generate one or more input signals based on a received audio signal;
   a signal processor configured to provide an output signal based on the one or more input signals;
   an output transducer configured to provide an audio output signal based on the output signal from the signal processor; and
   a time monitor configured to monitor an expiry time of a subscription for the hearing device;
   wherein the hearing device is configured to perform an action when the time monitor detects that the expiry time of the subscription is reached;
   wherein the hearing device is configured to connect with a program product as the action;
   wherein the hearing device is configured to receive a new expiry time of the subscription via the program product;
   wherein the program product is in an electronic device of the user, and wherein the hearing device is configured to connect with the program product in the electronic device of the user; and
   wherein the new expiry time of the subscription is provided by a server, and wherein the hearing device is configured to receive the new expiry time from the server via the program product in the electronic device of the user.

16. A server comprising:
   a non-transitory medium storing information relating to a subscription service for a hearing device, the hearing device configured to be arranged at an ear of a user;
   wherein the server is configured to communicate with a program product in an electronic device of the user;
   wherein the server is configured to provide the information for reception by the hearing device via the program product in the electronic device of the user, wherein the information is regarding a feature of the hearing device; and
   wherein the server is configured to receive payment information for the subscription service.

17. The server of claim 16, wherein the information is associated with a renewal or an upgrade of a functionality of the hearing device.

18. The server of claim 16, wherein the information comprises one or more parameters and/or algorithms for specifying and/or implementing a functionality for the hearing device.

19. The server of claim 16, wherein the server is configured to provide a new expiry time of subscription for the hearing device.

20. An electronic device comprising:
a communication interface configured to communicate with a hearing device, wherein the hearing device is configured to be arranged at an ear of a user; and
a processing unit;
wherein the electronic device is configured to receive information regarding a feature of the hearing device relating to a subscription service from a server, and to transmit the information to the hearing device; and
wherein the electronic device is configured to provide payment information for the subscription service.

21. The electronic device of claim 20, wherein the electronic device is also configured to connect to the server to check a subscription status of the hearing device.

22. The electronic device of claim 20, wherein the information is associated with a renewal or an upgrade of a functionality of the hearing device.

23. The electronic device of claim 20, wherein the information comprises one or more parameters and/or algorithms for specifying and/or implementing a functionality for the hearing device.

24. The electronic device of claim 20, wherein the electronic device is configured to receive a new expiry time of subscription for the hearing device from the server.

25. A method comprising:
communicating with a server to obtain information regarding a feature of a hearing device in relation to a subscription service;
connecting with the hearing device;
providing the information regarding the feature of the hearing device for transmission to the hearing device;
checking a subscription status of the hearing device;
obtaining payment information for the subscription service; and
providing the payment information for transmission to the server.

26. The method of claim 25, wherein the information is associated with a renewal or an upgrade of a functionality of the hearing device.

27. The method of claim 25, wherein the information comprises one or more parameters and/or algorithms for specifying and/or implementing a functionality for the hearing device.

28. The method of claim 25, further comprising receive a new expiry time of subscription for the hearing device, and transmitting the new expiry time for reception by the hearing device.

29. A program product having a processor-readable medium storing a set of instructions, an execution of which will cause the method of claim 25 to be performed.

* * * * *